(12) United States Patent
Heggs (10) Patent No.: US 7,651,866 B2
(45) Date of Patent: Jan. 26, 2010

(54) PURGE AND TRAP CONCENTRATOR WITH ELECTRICALLY ADJUSTED PURGE FLOW

(75) Inventor: Eric T. Heggs, Eaton, OH (US)

(73) Assignee: Teledyne Tekmar Company, Masonville, OH (US)

( * ) Notice: Subject to any disclaimer, the term of this patent is extended or adjusted under 35 U.S.C. 154(b) by 512 days.

(21) Appl. No.: 10/402,377

(22) Filed: Mar. 28, 2003

(65) Prior Publication Data

US 2004/0191126 A1  Sep. 30, 2004

(51) Int. Cl.
*G01N 30/06* (2006.01)
(52) U.S. Cl. .................... 436/178; 422/69; 422/70; 422/89; 422/101; 436/161
(58) Field of Classification Search ............ 422/69, 422/70, 89, 101; 436/161, 178
See application file for complete search history.

(56) References Cited

U.S. PATENT DOCUMENTS

| | | | | |
|---|---|---|---|---|
| 4,003,257 A | * | 1/1977 | Fletcher et al. | 73/19.02 |
| 5,322,626 A | * | 6/1994 | Frank et al. | 210/634 |
| 5,512,831 A | * | 4/1996 | Cisar et al. | 324/426 |
| 5,689,073 A | * | 11/1997 | DaPrato et al. | 73/863.01 |
| 5,792,423 A | * | 8/1998 | Markelov | 422/83 |
| 5,795,368 A | * | 8/1998 | Wright et al. | 95/82 |

* cited by examiner

*Primary Examiner*—Jan M Ludlow
(74) *Attorney, Agent, or Firm*—K&L Gates LLP (57) ABSTRACT

A purge and trap concentrator has a sample processing system that includes a network of fluid passageways and fluid control devices. A flow controller couples to a purge gas inlet provides an electrically adjustable purge gas flow rate as a function of an electrical input. A digital controller provides the system cycle and provides the electrical input. The electrical input varies as a function of the system cycle to increase the rate of flow of purge gas during a bake step relative to the rate of flow of purge gas during a purge step in the system cycle.

19 Claims, 7 Drawing Sheets

PURGE AND TRAP CONCENTRATOR WITH ELECTRICALLY ADJUSTED PURGE FLOW

FIELD OF THE INVENTION

The present invention relates generally to purge and trap concentrators. In particular, the present invention relates to purge and trap concentrators that can be connected to gas chromatographs.

BACKGROUND OF THE INVENTION

A purge and trap concentrator, such as the Tekmar-Dohrmann Velocity XPT Sample Concentrator, receives a liquid sample that typically includes volatile compounds. When the purge and trap concentrator passes a purge gas through the sample, volatile compounds are purged from the liquid as gas or vapor and trapped in a trap. The trapped volatile compounds are then transferred to a gas chromatograph or other chemical analysis instrument for chemical analysis. The purge and trap concentrator can heat the liquid sample to a precisely reproducible temperature to improve extraction of volatile organic compounds (VOCs) and ensure repeatability of the chemical analysis. The analysis cycle time needed to inject a liquid sample, heat it to the correct temperature, purge the volatile sample from the liquid, drain the purge and trap concentrator, and bake and cool the trap to prepare it for the next sample sets a limit on the rate at which the purge and trap concentrator can complete processing of multiple samples. In an environment where samples can be delivered at a high rate, and a high speed gas chromatograph or other gas analyzer can analyze samples at a high rate, the purge and trap concentrator becomes a limiting factor or bottleneck for production speed. There is a need to reduce the analysis cycle time of the purge and trap concentrator to improve productivity in chemical analysis of volatile compounds.

SUMMARY OF THE INVENTION

Disclosed are a purge and trap concentrator and a method of cycling a purge and trap concentrator. The purge and trap concentrator includes a sample processing system that includes a plurality of fluid control devices and a network of fluid passageways interconnecting the fluid control devices. The purge and trap concentrator also includes a sample inlet adapted to receive a chemical sample and a sample outlet adapted to provide a concentrated chemical sample. The sample processing system operates according to a system cycle of a sequence of processing steps including at least a purge step, a desorption step and a bake step.

A purge gas inlet to the sample processing system receives purge gas. A flow controller coupled to the purge gas inlet provides an electrically adjustable rate of flow of the purge gas to the sample processing system as a function of an electrical input.

A digital controller provides the system cycle and provides the electrical input. The electrical input varies as a function of the system cycle to increase the rate of flow of purge gas during the bake step relative to the rate of flow of purge gas during the purge step.

These and various other features as well as advantages that characterize the present invention will be apparent upon reading of the following detailed description and review of the associated drawings.

DETAILED DESCRIPTION OF ILLUSTRATIVE EMBODIMENTS

In the embodiments described below, a purge and trap concentrator and method are disclosed that provide reduced cycle time for each complete purge and trap cycle. A flow controller in the purge and trap concentrator adjusts a rate of flow of purge gas to the purge and trap concentrator depending on which step (mode) of the cycle is being performed. The flow controller can be a mass flow controller, an arrangement of flow restrictors and electrically actuated valves, or other electrically controllable flow control device. For example, the flow of purge gas can be adjusted to a standard lower level of about 40 ml/min during a purge step to meet standard US EPA 524.2 and adjusted to a higher level of about 320-400 ml/min during a bake step to reduce the time needed to complete the bake step from a standard 8-12 minutes down to about 2 minutes. The overall cycle time of the purge and trap concentrator is reduced from 25-35 minutes down to about 15-18 minutes. With this greatly reduced cycle time, the purge and trap concentrator can cycle faster than a high speed gas chromatograph and allows the full capability of the high speed gas chromatograph to be utilized.

Daily production throughput of sample processing is increased because processed chemical samples are delivered to a gas chromatograph at a high enough rate so that the speed of the gas chromatograph is not limited by the speed of the purge and trap concentrator.

In typical purge and trap concentrators, cycle times are about 25-35 minutes. This includes a purge step (11 minutes), dry purge step (0-6 minutes), desorb preheat step (0-1.5 minutes), desorb step (2-4 minutes), bake step (8-12 minutes), and trap cooldown step (2 minutes). In the past the subsequent gas chromatograph (GC) analysis was slow and was the limiting factor on how many samples could be analyzed by a single combined purge and trap concentrator—gas chromatograph system. The method of analysis of a complex mixture such as US EPA Method 524.2 required about 40-60 minutes. This included a separation time of about 30-45 minutes and an oven cooldown time of about 10-15 minutes). In a system with an older GC, the purge and trap concentrator was waiting idle for up to 35 minutes of every hour. Recent Advances in GC column technology have drastically decreased the time needed for the GC to analyze the same complex mixtures.

Current column technology will allow separation of a complete list according to standard US EPA 524.2 in 17 minutes, yielding a total GC cycle time of 25 minutes. When this new faster column technology is implemented in a GC, the limiting factor to the number of samples that can be analyze in a day shifts from the GC to the slower purge and trap concentrator.

When the cycle time for a purge and trap concentrator is broken down into its individual steps or modes, there are two major tasks that consume the majority of the time. The purge step which is about 11 minutes and the bake step which is about 8-12 minutes of the cycle time. The purge time is strictly regulated by the US EPA method due to the fact that reducing the purge time could drastically reduce the sensitivity of the purge and trap concentrator-gas chromatograph system if the flow rates are not increased proportionally. Increasing the purge flow rate will increase the linear velocity of the purge gas through the trap which will result in less efficient concentrator of the target compounds. Recognizing these difficulties and the complexity of having the US EPA method amended, a method of decreasing time spent on the other purge and trap functions is disclosed here.

To decrease the purge and trap cycle time, an electrically controllable flow controller is used, rather than a manually settable mechanical flow controller. The use of the electrically controllable flow controller allows the purge gas flow rates to be changed for specific modes of operation. With the mechanical flow controller, there was no automatic adjustment to the flow rate at the purge gas inlet, and the purge and trap concentrator could only use the same flow rate for all modes, thus increasing the times required to complete a cycle. The flow controller allows for the purge flow rate of 40 ml/min (specified by the USEPA) as well as flows up to 500 ml/min. Typically 320-400 ml of flow is passed through the analytical trap during the bake mode to regenerate it prior to analyzing the next sample. On a standard purge and trap concentrator this requires about 8-10 minutes, but utilizing the variable flow capability of the flow controller allows the system to pass more than twice the amount of flow in as little as about 2 minutes. The result of this increased flow rate and decreased time is a throughput increase of 6-8 minutes. The same technique can be applied to the dry purge mode, if applicable for the trapping materials and methodology. The utilization of the flow controller will allow the purge and trap cycle time to be reduced to about 15-18 minutes (Purge 11 minutes, Dry Purge 0-1 minutes, Desorb Preheat 0-1 minute, Desorb 1-2 minutes, Bake 2 minutes and Trap Cooldown 1 minute) without compromising the analysis. This change to the flow can result in an efficiency increase of approximately 45%. The flow controller can be a mass flow controller (MFC), an arrangement of flow restrictors and electrically actuated valves, or other electrically adjustable flow control arrangements that can provide different purge flows in different modes.

Figure 1:
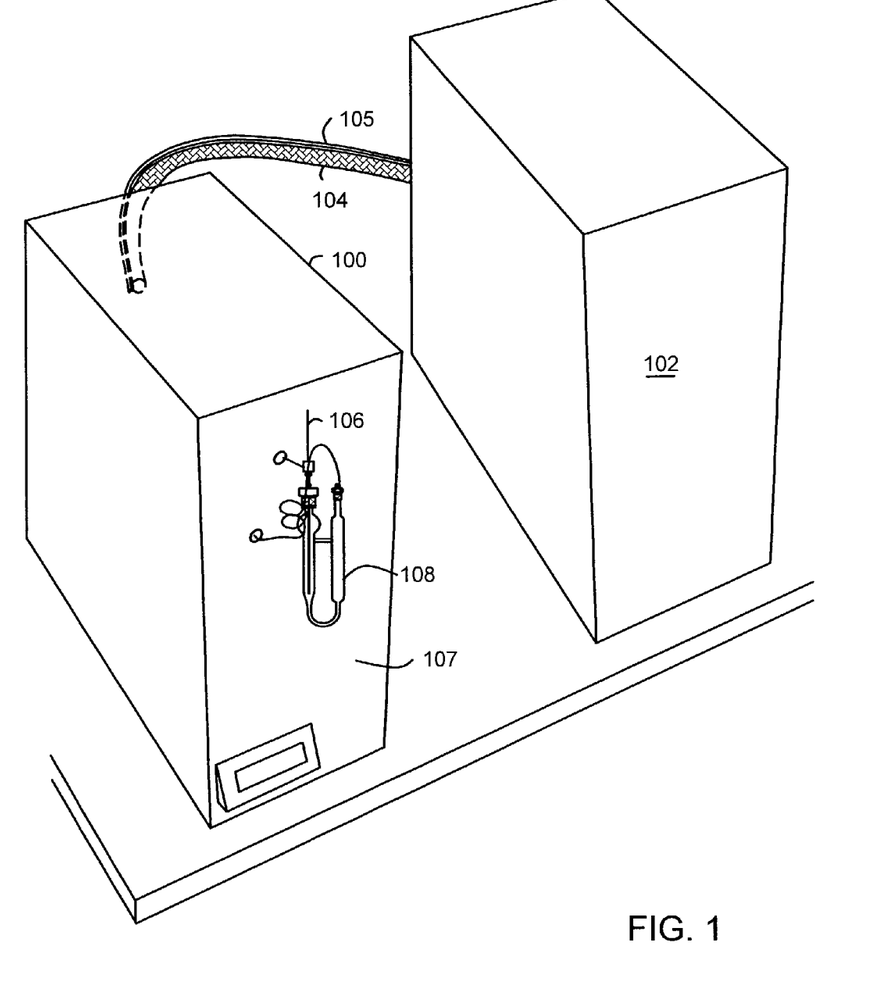
FIG. 1 illustrates a purge and trap concentrator connected to a gas chromatograph.

FIG. 1 illustrates a purge and trap concentrator 100 connected to a gas chromatograph 102 by a heated outlet line 104. A carrier gas line 105 is secured to an outer sheath of the heated outlet line 104 and couples from the gas chromatograph 102 to the purge and trap concentrator 100. The purge and trap concentrator 100 performs purge and trap functions on chemical samples. The purge and trap concentrator has a sample inlet 106. Typically, a chemical sample is injected at inlet 106 using a syringe (not illustrated). The injected chemical sample is received in a sparging tube 108 that is part of the purge and trap concentrator 100, but is mounted externally on front panel 107 for easy access. The chemical sample is processed in the purge and trap concentrator 100 and then a concentrated chemical sample is coupled via the heated outlet line 104 to the gas chromatograph 102. The purge and trap concentrator cycles through a control cycle that includes steps that are explained below in connection with an example shown in FIG. 2. If desired, the purge and trap concentrator 100 in FIG. 1 can be connected to an autosampler (not illustrated).

Figure 2:
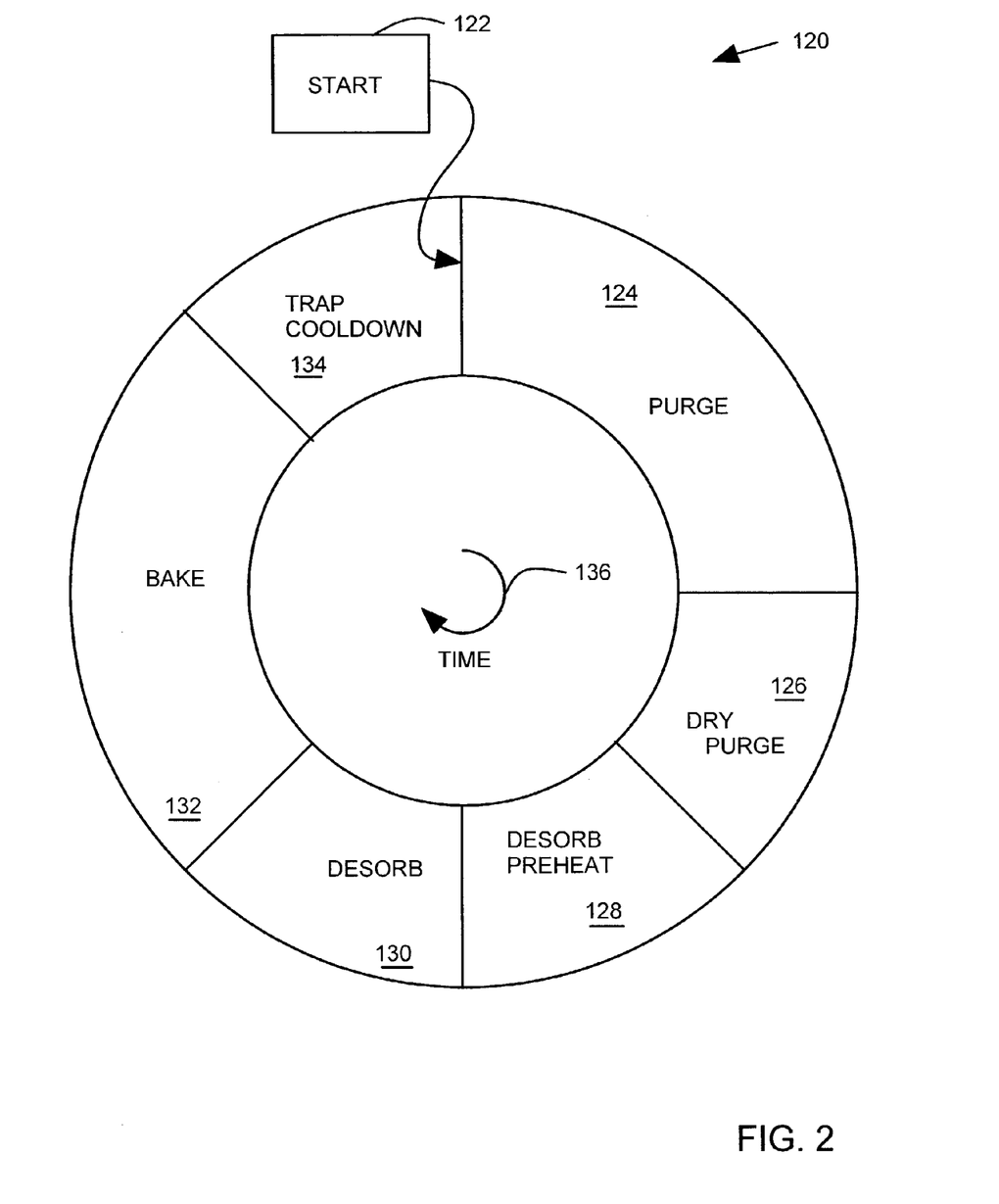
FIG. 2 illustrates sequential operation modes in a system cycle of a purge and trap concentrator.

FIG. 2 schematically illustrates a system cycle 120 of sequential steps or modes in a purge and trap concentrator such as purge and trap concentrator 100 in FIG. 1 or purge and trap concentrators described below in connections with FIGS. 3-7. The system cycle or ring sequence 120 starts at start 122 and moves sequentially through a purge mode 124, a dry purge mode 126, a desorb preheat mode 128, a desorb mode 130, a bake mode 132 and a trap cooldown mode 134. Upon completion of the trap cooldown mode 134, the purge and trap concentrator is ready to begin another system cycle 120 with the next sample. As indicated by central arrow 136 at the center of the ring sequence 120, time elapses in a clockwise direction. A sequence of steps in the ring sequence 120 is cyclical or repetitive. The ring 120 illustrates the sequence of steps for processing a single sample in the purge and trap concentrator. It is important to note that the length of time of the bake mode 132 is greatly reduced by increasing flow of purge gas during the bake cycle, as explained in more detail in the examples illustrated below in FIGS. 3-7. In a preferred arrangement, the length of time of the dry purge cycle 126 is also reduced by increasing flow of purge gas during the dry purge cycle.

Figure 3:
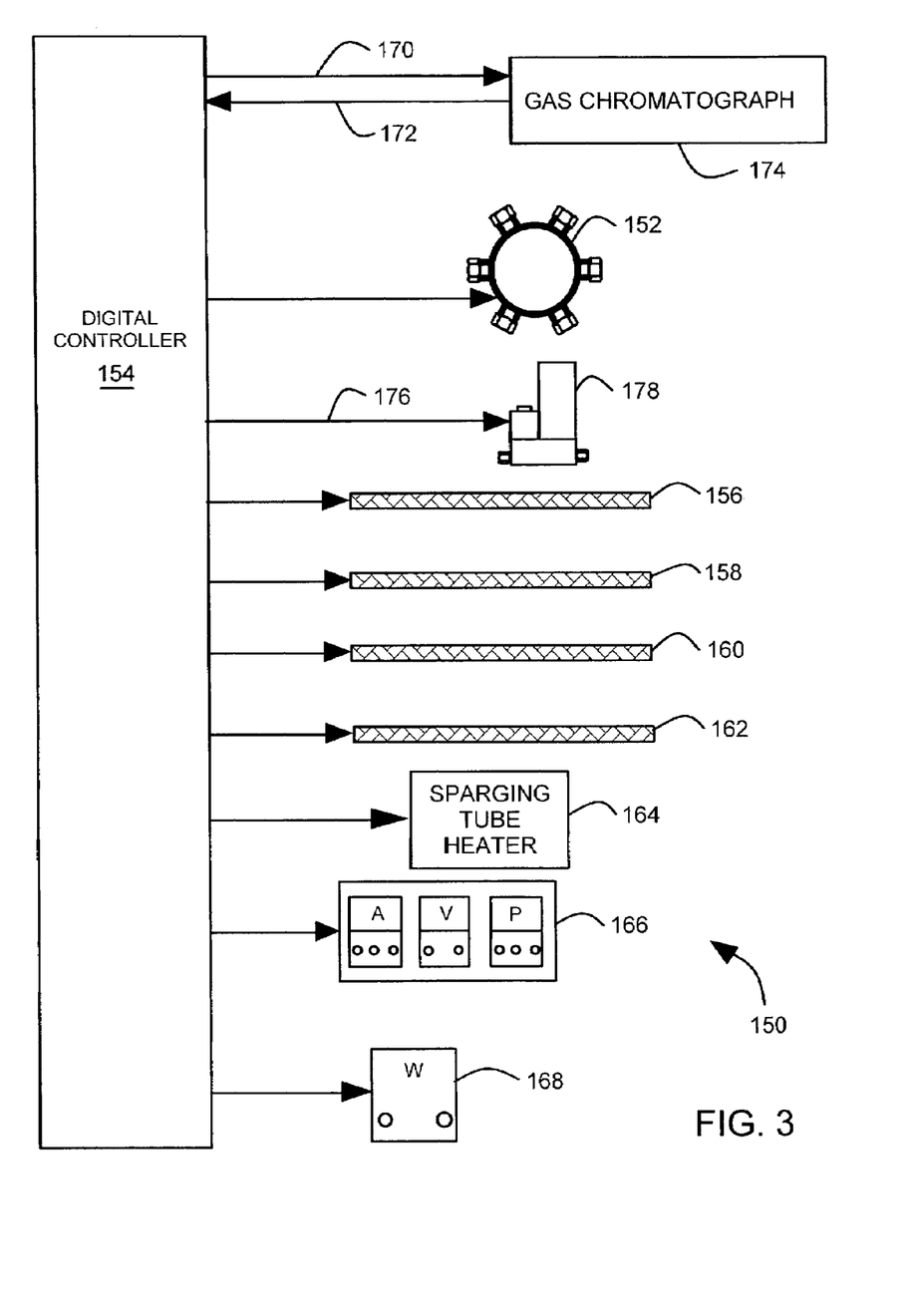
FIG. 3 schematically illustrates a block diagram of electrical connections in a purge and trap concentrator.

FIG. 3 schematically illustrates a block diagram 150 of electrical connections in a purge and trap concentrator. A digital controller 154 automatically actuates fluid control devices such as a 6 port valve 152, a valve manifold 166 and a drain valve 168. As understood by those of ordinary skill in the art, the six port valve 152 may be actuated between two positions and to route gas through the various parts of the unit. The digital controller 154 also actuates a trap heater 156, a water control system heater 158, an outlet line heater 160, a line heater 162, and a sparging tube heater 164. The digital controller 154 can also control other devices (not illustrated) as well, such as an oven for the six port valve 152 or a sample mount heater, and can receive data from temperature sensors (not illustrated). External connections 170, 172 are provided so that the digital controller 154 can communicate with a gas chromatograph 174 to synchronize the operation of the purge and trap concentrator with the operation of the gas chromatograph 174. The digital controller 154 also provides an electrical input 176 to a mass flow controller 178. The mass flow controller 178 adjusts the flow of purge gas as a function of the electrical input 176. The electrical input 176 can be analog or digital and provides an indication to the mass flow controller of a desired flow rate for the purge gas flow.

The digital controller provides a time sequence or system cycle (such as the one illustrated in FIG. 2). The electrical input 176 varies as a function of the system cycle to increase the rate of flow of purge gas during a bake step relative to the rate of flow of purge gas during a purge step. In a preferred arrangement, the electrical input 176 can also vary to increase the rate of flow of purge gas during a dry purge step. These increased rates of flow decrease the cycle time of the purge and trap concentrator. The digital controller 154 typically comprises a microprocessor system with I/O devices interfacing with the various valves, heaters, the mass flow controller 178 and the gas chromatograph 174. Fluid handling aspects of the purge and trap concentrator illustrated in FIG. 3 are described in more detail below in connection with FIGS. 4-5.

Figure 4:
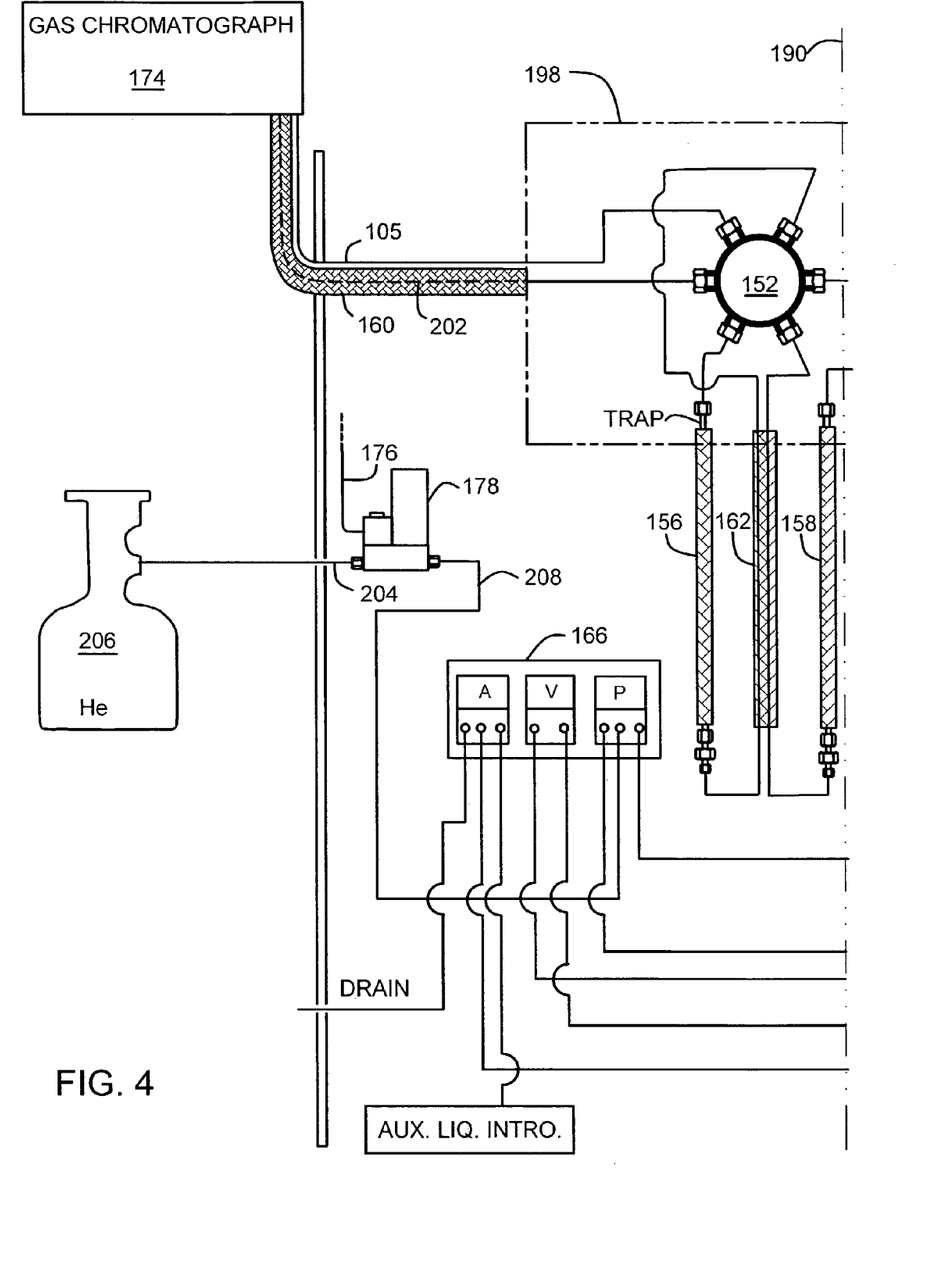
FIGS. 4-5, taken together, schematically illustrates a block diagram of fluid handling in a purge and trap concentrator connected to a gas chromatograph.
Figure 5:
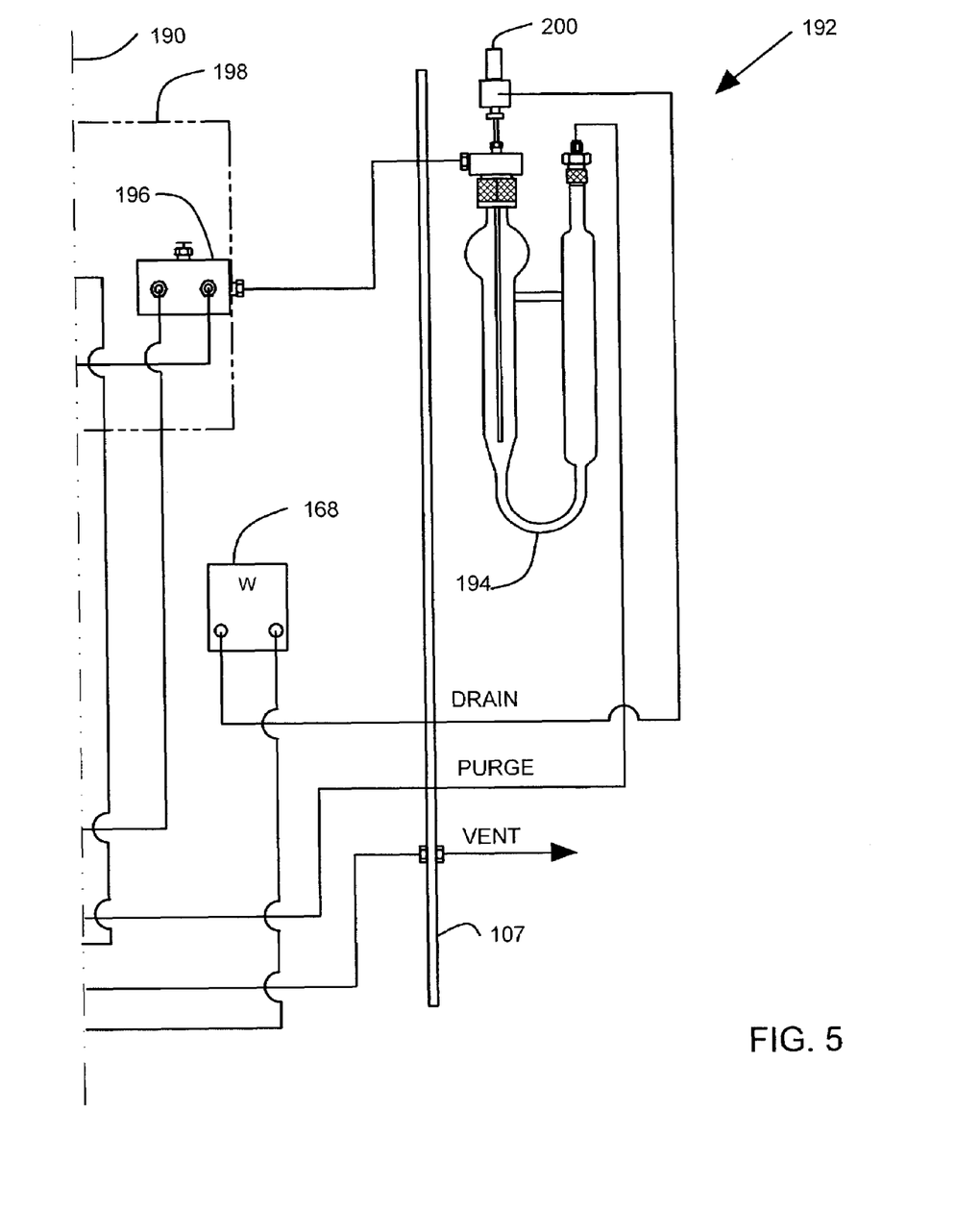

FIGS. 4-5, taken together, schematically illustrates a block diagram of fluid handling in a purge and trap concentrator connected to a gas chromatograph 174. For convenience in reading FIGS. 4-5, the right edge of FIG. 4 can be joined with the left edge of FIG. 5 along broken line 190 in each of FIGS. 4-5.

The purge and trap concentrator includes a sample processing system 192 comprising a plurality of fluid control devices 152, 166, 168 and 194. Fluid control device 194 comprises a heated sparging tube. A network of fluid passageways (illustrated by solid lines) interconnect the fluid control devices 152, 166, 168 and 194. Some of the interconnecting lines and other devices are heated as indicated by heater jackets with a herringbone pattern in FIGS. 4-5. The 6 port valve 152 and a four way tee valve 196 are placed in a heated valve oven 198. A sample inlet 200 is arranged to receive a chemical sample. A sample outlet 202 (inside outlet line heater 160) is arranged to provide a concentrated chemical sample to the gas chromatograph 174. The sample processing system 192 operates according to a system cycle of a sequence of processing steps such as the example illustrated in FIG. 2.

A purge gas inlet 204 is arranged to receive purge gas from a gas tank 206 that is typically external to the purge and trap concentrator. The mass flow controller 178 couples to the purge gas inlet 204 and provides an electrically adjustable rate of flow of the purge gas on line 208 to the valve manifold 166 in the sample processing system 192. The rate of flow of purge gas is adjustable automatically as a function of the electrical input 176 that is provided by the digital controller 154 described above in connection with FIG. 3.

The mass flow controller (MFC) 178 can be a commercially available flow controller, for example, of the type used to control the flow of gasses in semiconductor manufacturing processes. The mass flow controller 178 typically includes a mass flow sensor, a valve and a control circuit that receives the electrical input 176 as a set point and controls the valve as a function of a difference between the set point and an output from the mass flow sensor. In a preferred arrangement, the rate of flow of the purge gas is increased during the bake step so that the bake step can be reduced to about 2 minutes in length and the system cycle is reduce to about 18 minutes. In another preferred arrangement, the rate of flow during the purge step is adjusted to about 35-45 ml/min, and the rate of flow during the bake step is adjusted to 320-400 ml/min.

The gas chromatograph 174 connected to the sample outlet 202 has a measurement cycle time. With the arrangement illustrated in FIGS. 3-5, the system cycle of the purge and trap concentrator is shorter than a measurement cycle time.

Figure 6:
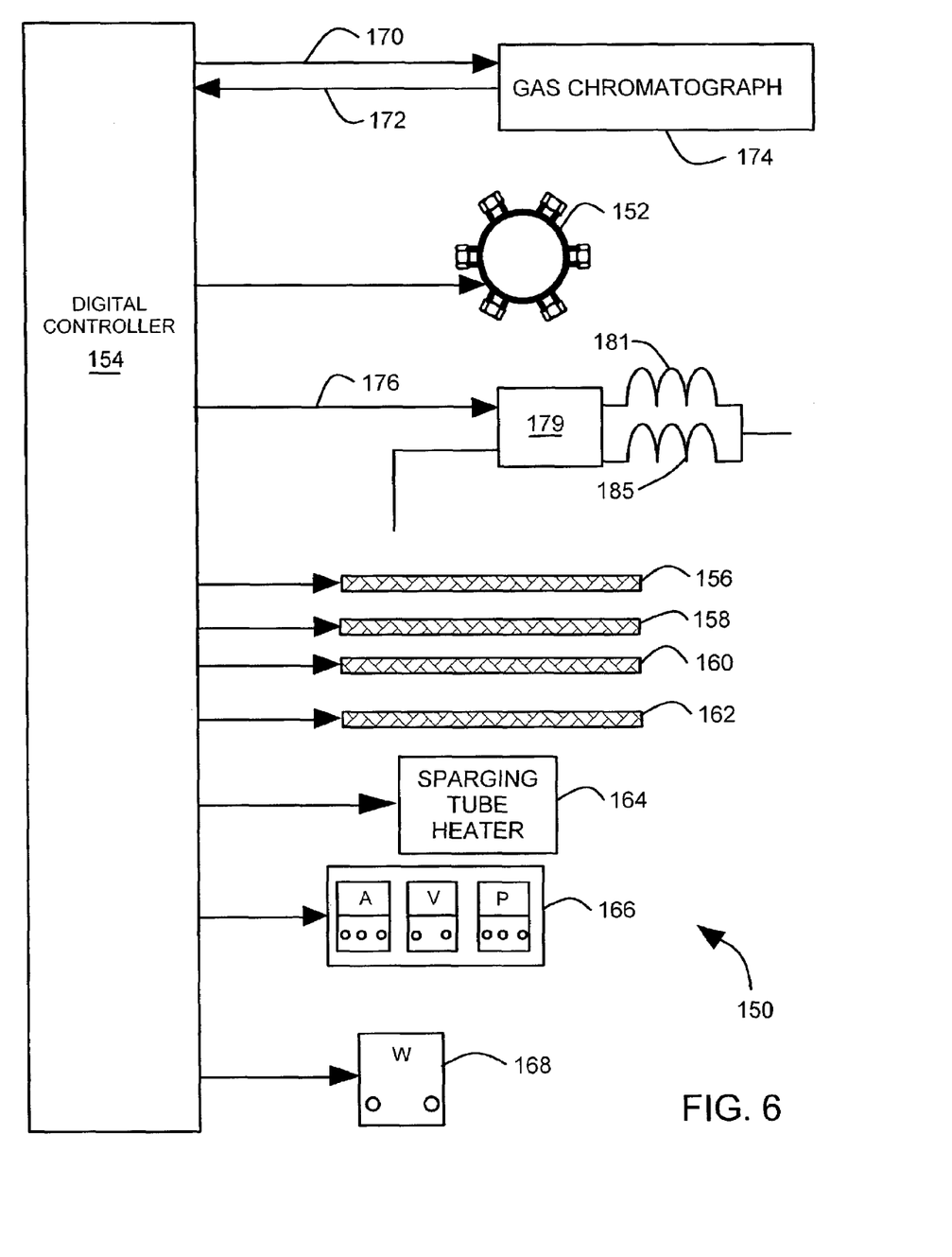
FIG. 6 schematically illustrates connections from a digital controller to a valve controlling purge flow in a purge and trap concentrator.

FIG. 6 schematically illustrates connections from a digital controller 154 to a three way valve 179 controlling purge flow in a purge and trap concentrator. The arrangement illustrated in FIG. 6 is similar to the arrangement illustrated in FIG. 3 and reference numbers used in FIG. 6 that are the same as reference numbers used in FIG. 3 identify the same or similar features. The arrangement illustrated in FIG. 6 uses an electrically actuated three way valve 179 and flow restrictors 181, 185 to adjust a rate of flow of purge gas rather than using the mass flow controller 178 shown in FIG. 3.

Figure 7:
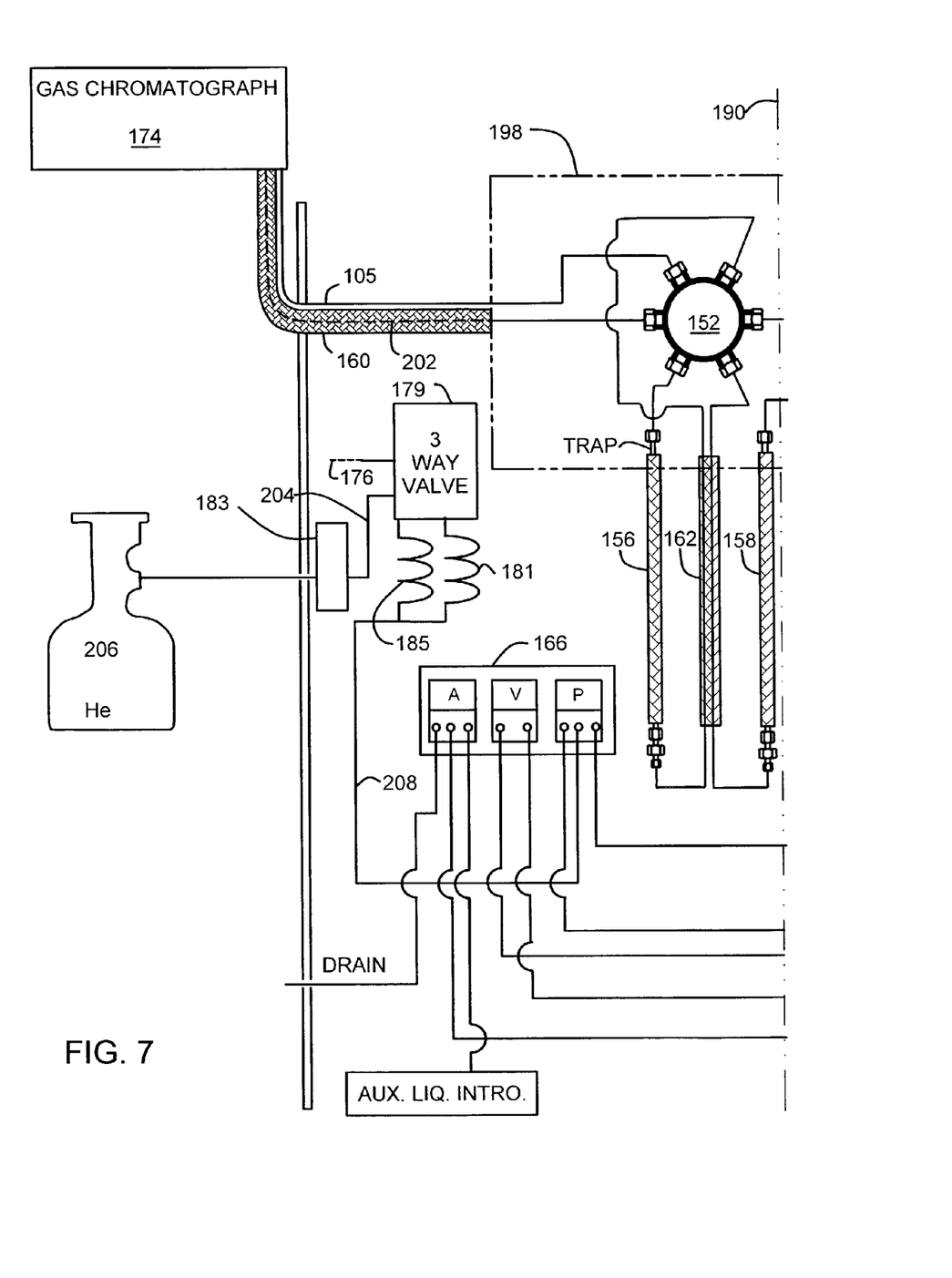
FIG. 7, taken together with FIG. 5, schematically illustrates a block diagram of a purge and trap concentrator connected to a gas chromatograph.

FIG. 7, taken together with FIG. 5, schematically illustrates a block diagram of flow paths in the purge and trap concentrator illustrated in FIG. 6. The arrangement illustrated in FIG. 7 is similar to the arrangement illustrated in FIG. 4 and reference numbers used in FIG. 7 that are the same as reference numbers used in FIG. 4 identify the same or similar features. The arrangement illustrated in FIG. 7 uses the electrically actuated three way valve 179 and the flow restrictors 181, 185 to adjust a rate of flow of purge gas rather than using the mass flow controller 178 as shown in FIG. 4. Flow restrictor 181 has a resistance to flow that is different than that of flow restrictor 185. The three way valve 179 allows gas to flow through a selected one of the flow restrictors 181, 185 to provide a selectable flow rate. In a preferred arrangement, a mechanical regulator 183 provides a controlled pressure at the inlets of the valve 179 and the flow restrictor 181. The valve 179 and the flow restrictors 181, 185 together comprise a flow controller for controlling flow of purge gas, and the flow controller is automatically electrically controlled by an electrical input 176.

In a further preferred arrangement, the flow controller can comprise a single flow restrictor and an electrically actuatable valve bypassing the single flow restrictor to provide a selectable flow rate.

It is to be understood that even though numerous characteristics and advantages of various embodiments of the invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, the particular elements may vary depending on the particular application for the purge and trap while maintaining substantially the same functionality without departing from the scope and spirit of the present invention. For example, the purge and trap can be used with other know standard test methods in addition to US EPA Method 524.2. In addition, although the preferred embodiment described herein is directed to purge and trap concentrators, it will be appreciated by those skilled in the art that other types of concentrators can be implemented as well. The teachings of the present invention can be applied to other chemical processing instruments without departing from the scope and spirit of the present invention.

What is claimed is:

1. A purge and trap concentrator, comprising:
a sample processing system operating according to a system cycle of a sequence of processing steps including at least a purge step, a desorption step and a bake step, the sample processing system comprising:
a sparger having a sample inlet adapted to receive a chemical sample;
a trap in fluid communication with the sparger through a two-position valve;
a valve manifold comprising
a vent valve in fluid communication with a vent the sparger and the trap, and
a purge valve in fluid communication with a purge gas inlet adapted to receive a purge gas and the sparger;
a sample outlet in fluid communication with the two-position valve; and
a heated valve in fluid communication with the sparger, the purge valve, and the trap;
wherein the valve manifold and the two-position valve control the distribution of gas flow through the sample processing system in different flow paths as a function of electrical inputs;
an electronic flow controller in fluid communication with the purge gas inlet at an inlet to the flow controller, and in fluid communication with a purge gas inlet of the valve manifold at an outlet from the flow controller, wherein the flow controller is configured to control the flow of purge gas delivered to the sample processing system, and wherein the flow controller provides an electrically adjustable rate of flow of the purge gas to the valve manifold in the sample processing system as a function of an electrical input wherein the electronic flow controller allows the rate of flow of the purge gas to be changed for specific modes of operation of the sample processing system; and a digital controller providing the system cycle and providing the electrical inputs to at least the flow controller, the valve manifold and the two-position valve, the electrical inputs varying as a function of the system cycle to automatically change the flow path of the purge gas between system cycle steps and to automatically increase the rate of flow of purge gas during the bake step relative to the rate of flow of purge gas during the purge step.

2. The purge and trap concentrator of claim 1 wherein the increased rate of flow of the purge gas during the bake step reduces the bake step to about 2 minutes.

3. The purge and trap concentrator of claim 2 wherein the increased rate of flow of purge gas during the bake step reduces the system cycle to about 18 minutes.

4. The purge and trap concentrator of claim 1 wherein the flow controller comprises a mass flow controller (MFC).

5. The purge and trap concentrator of claim 1 wherein the flow controller comprises a flow restrictor and an electrically actuated valve.

6. The purge and trap concentrator of claim 1 wherein the flow controller comprises a plurality of flow restrictors and an electrically actuated valve.

7. The purge and trap concentrator of claim 1 wherein the rate of flow during the purge step is adjusted to about 35-45 ml/min.

8. The purge and trap concentrator of claim 1 wherein the rate of flow during the bake step is adjusted to 320-400 ml/min.

9. The purge and trap concentrator of claim 1 further comprising a gas chromatograph connected to the sample outlet, the system cycle being shorter than a measurement cycle of the gas chromatograph.

10. The purge and trap concentrator of claim 1 wherein the system cycle includes a dry purge step and the electrical input varies as a function of the system cycle to increase the flow rate of purge gas during the dry purge step relative to the rate of flow of purge gas during the purge step.

11. A method of concentrating a chemical sample, comprising:

providing a sample concentrating system operating according to a system cycle of a sequence of processing steps including at least a purge step, a desorption step and a bake step, the sample processing system comprising:
  a sparger having a sample inlet adapted to receive a chemical sample;
  a trap in fluid communication with the sparger through a two-position valve;
  a valve manifold comprising
    a vent valve in fluid communication with a vent the sparger and the trap, and
    a purge valve in fluid communication with a purge gas inlet adapted to receive a purge gas and the sparger;
  a sample outlet in fluid communication with the two-position valve;
  a heated valve in fluid communication with the sparger, the purge valve, and the trap;
  an electronic flow controller in fluid communication with the purge gas inlet at an inlet to the flow controller, and in fluid communication with a purge gas inlet of the valve manifold at an outlet from the flow controller;
  wherein the valve manifold and the two-position valve control the distribution of gas flow through the sample processing system in different flow paths as a function of electrical inputs, and wherein the electronic flow controller electrically provides an adjustable rate of flow of purge gas to the valve manifold in the sample processing system as a function of an electrical input, wherein the electronic flow controller allows the rate of flow of the purge gas to be changed for specific modes of operation of the sample processing system;

providing the system cycle to the sample concentrating system and providing electrical inputs to the flow controller, the valve manifold and the two-position valve, the electrical inputs provided by the digital controller and varying as a function of the system cycle; and providing a flow of a purge gas to the concentrating system that is electrically adjustable as a function of the electrical input to the flow controller to automatically increase the rate of flow of purge gas during the bake step in the system cycle relative to the rate of flow of purge gas during the purge step in the system cycle.

12. The method of claim 11 further comprising coupling the electrical input to a mass flow controller (MFC) that adjusts the rate of flow.

13. The method of claim 11 further comprising adjusting the rate of flow with a flow restrictor and an electrically actuated valve coupled to the flow restrictor.

14. The method of claim 11 further comprising adjusting the rate of flow with a plurality of flow restrictors and an electrically actuated valve coupled to the flow restrictors.

15. The method of claim 11 further comprising adjusting the rate of flow during the purge step to about 40 ml/min.

16. The method of claim 11 further comprising adjusting the rate of flow during the bake step to 320-400 ml/mm, and completing the bake step in about 2 minutes.

17. The method of claim 11 further comprising completing the system cycle in about 18 minutes.

18. The method of claim 11 further comprising connecting a gas chromatograph to the sample outlet to shorten the purge and trap system to less than a measurement cycle of the gas chromatograph.

19. The method of claim 11 wherein the system cycle includes a dry purge step and the electrical input varies as a function of the system cycle to automatically increase the flow rate of purge gas during the dry purge step in the system cycle relative to the rate of flow of purge gas during the purge step in the system cycle.

* * * * *

UNITED STATES PATENT AND TRADEMARK OFFICE
CERTIFICATE OF CORRECTION

PATENT NO. : 7,651,866 B2
APPLICATION NO. : 10/402377
DATED : January 26, 2010
INVENTOR(S) : Eric T. Heggs It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 749 days.

Signed and Sealed this

Twenty-third Day of November, 2010

David J. Kappos
*Director of the United States Patent and Trademark Office*